US010688015B2

(12) United States Patent
Pounders

(10) Patent No.: US 10,688,015 B2
(45) Date of Patent: *Jun. 23, 2020

(54) APPARATUS FOR SIMULATING SEXUAL MOTION

(71) Applicant: MB Technologies LLC, Sanford, NC (US)

(72) Inventor: John Pounders, Nashville, TN (US)

(73) Assignee: MB Technologies, LLC, Sanford, NC (US)

( * ) Notice: Subject to any disclaimer, the term of this patent is extended or adjusted under 35 U.S.C. 154(b) by 209 days.

This patent is subject to a terminal disclaimer.

(21) Appl. No.: 15/877,279

(22) Filed: Jan. 22, 2018

(65) Prior Publication Data

US 2019/0015293 A1 Jan. 17, 2019

Related U.S. Application Data

(63) Continuation-in-part of application No. 15/688,517, filed on Aug. 28, 2017, now Pat. No. 10,500,126.

(Continued)

(51) Int. Cl.

*A61F 5/00* (2006.01)
*A61H 19/00* (2006.01)
*A61H 23/02* (2006.01)

(52) U.S. Cl.

CPC ............. *A61H 19/40* (2013.01); *A61H 19/00* (2013.01); *A61H 19/32* (2013.01); *A61H 19/44* (2013.01);

(Continued)

(58) Field of Classification Search

CPC ........ A61H 19/00; A61H 19/30; A61H 19/40; A61H 19/44; A61H 19/50

(Continued)

(56) References Cited

U.S. PATENT DOCUMENTS 4,349,708 A * 9/1982 Asher ................ G05G 9/04788 200/17 R
7,267,646 B2 * 9/2007 Tucker .................. A61H 19/44 600/38

(Continued)

*Primary Examiner* — John P Lacyk

(57) ABSTRACT

Provided is an apparatus for producing a motion to be felt by a user comprising; a) a motor for generating a motion; b) a first member mechanically coupled to the motor, the member configured to have a motion of up and down; and c) a second member mechanically coupled to the first member and attached to a fixed location on the apparatus, the second member configured to tilt as a result of the motion of the first member; wherein the user has an option of choosing to experience the up and down motion generated by the first member or the tilting motion generated by the second member. The first and the second member can be each configured to receive a different extension, each extension configured to penetrate a body of the user. Provided is an apparatus for producing a motion to be felt by a user comprising; a) a motor for generating a motion; b) a cam with a groove going around the cam mechanically couple to the motor, the cam rotating as a result of motion from the motor; c) a slider mechanically coupled to the cam with the groove, the slider moving up and down as the cam rotates; d) a rod attached to the slider, the rod moving up and down with the slider, a first member mechanically coupled to the motor, the member configured to have a motion of up and down; wherein the rod moves up and down as the motor generates motion.

14 Claims, 11 Drawing Sheets

Related U.S. Application Data

(60) Provisional application No. 62/533,616, filed on Jul. 17, 2017.

(52) U.S. Cl.
CPC ......... *A61H 19/50* (2013.01); *A61H 23/0254* (2013.01); *A61H 19/34* (2013.01); *A61H 2201/0149* (2013.01); *A61H 2201/1215* (2013.01); *A61H 2201/1418* (2013.01); *A61H 2201/169* (2013.01); *A61H 2201/1633* (2013.01); *A61H 2201/1669* (2013.01); *A61H 2201/1673* (2013.01); *A61H 2201/1685* (2013.01); *A61H 2201/5053* (2013.01); *A61H 2201/5097* (2013.01); *A61H 2205/087* (2013.01)

(58) Field of Classification Search
USPC ...................................................... 600/38–41
See application file for complete search history.

(56) References Cited

U.S. PATENT DOCUMENTS 7,438,681 B2 * 10/2008 Kobashikawa ........ A61H 19/34 600/38
2015/0272739 A1 * 10/2015 Darnell ..................... A61F 2/26 600/40

* cited by examiner

APPARATUS FOR SIMULATING SEXUAL MOTION

CROSS-REFERENCE

The present application claims the benefit of U.S. provisional application No. 62/533,616, filed on Jul. 17, 2017, and a CIP of U.S. application Ser. No. 15/688,517, filed on 62/533,616, both of which are incorporated herein by reference in its entirety.

BACKGROUND SECTION OF THE INVENTION

Some people use an apparatus that simulates a sexual movement. A problem with these apparatus is that they generate a limited number of motions. There is a need in the art for apparatuses that generate additional kinds of motions.

SUMMARY SECTION OF THE INVENTION

Provided is an apparatus for producing a motion to be felt by a user comprising; a) a motor for generating a motion; b) a first member mechanically coupled to the motor, the member configured to have a motion of up and down; and c) a second member mechanically coupled to the first member and attached to a fixed location on the apparatus, the second member configured to tilt as a result of the motion of the first member, wherein the user has an option of choosing to experience the up and down motion generated by the first member or the tilting motion generated by the second member. The first and the second member can be each configured to receive a different extension, each extension configured to penetrate a body of the user. The apparatus can further comprise a silicone cover for placing over the extension. A user can feel a different motion depending on a type of extension. The first member can be in form of a rod. At least a portion of the second member can be circular, the circular portion configured to receive an extension. The first member can be attached to a base, the base forming a joint with the second member. The base can remain in a horizontal position regardless of a position of the first member. The first member can be mechanically coupled to a slider, the slider moving up and down. The slider ca ne mechanically coupled to a cam, moving up and down as the cam rotates. The cam can have a groove that goes around the cam, the groove going from bottom to top of the cam and then top to bottom to make a complete circle. The slider can have a guide that goes inside the groove, and moves the slider up and down as the cam rotates. The cam can be mechanically connected to a gear box. The cover can have a curved top configured for a user to sit on. The apparatus can further comprise a second motor, the second motor configured to generate a vibrating motion. The second motor can be coupled to a roller with a chain, the roller turning a shaft. The shaft can go through one or more openings on side of a frame, the frame having an additional opening for passage of the first member, wherein rotation of the shaft creates a vibratory motion in the frame.

Provided is an apparatus for producing a motion to be felt by a user comprising; a) a motor for generating a motion; b) a cam with a groove going around the cam mechanically couple to the motor, the cam rotating as a result of motion from the motor; c) a slider mechanically coupled to the cam with the groove, the slider moving up and down as the cam rotates; d) a rod attached to the slider, the rod moving up and down with the slider, a first member mechanically coupled to the motor, the member configured to have a motion of up and down; wherein the rod moves up and down as the motor generates motion. The apparatus can have a second motor for generating a vibrational motion, the second motor coupled to a roller with a chain, the roller turning a shaft that creates vibrational motion in at least one member of the apparatus. The apparatus can have a horizontal base for attaching the rod, the horizontal base forming a joint with a receiver at one end, the receive movably attached to fixed location on the apparatus, the receiver tilting back and forth as the rod moves up and down, wherein the user has an option of choosing to experience the up and down motion generated by the rod or the tilting motion generated by the receiver.

Provided is a cover for an apparatus configured to produce a motion; the cover comprising: a) a shaft; b) a body; c) a cavity all around the shaft, and in between the shaft and the body, wherein the shaft is movable in relation to the body when a force is applied to the shaft from a bottom of the cover. The shaft can have an opening inside that is configured to receive a portion of the apparatus. The body can have a snap cavity on a bottom side configured for removable attached to the apparatus. The shaft can be configured to move up and down, or sideways. The cover can be made from silicone. The body can be in form of two arms that extend on each side of the shaft. The shape of the cavity can change at the shaft moves.

Provided is an apparatus for producing a motion to be felt by a user comprising; a) a motor for generating a motion; b) a first member mechanically coupled to the motor, the member configured to have a motion of up and down; c) a second member mechanically coupled to the first member and attached to a fixed location on the apparatus, the second member configured to tilt as a result of the motion of the first member; d) an extension attached to the first or the second member; e) a cover placed on top of the extension, the cover having a shaft, a body, and a cavity all around the shaft, the shaft having an opening for receiving the extension; wherein the user has an option of choosing to experience the up and down motion generated by the first member or the tilting motion generated by the second member. The shaft can have an opening inside that is configured to receive a portion of the apparatus. The body can have a snap cavity on a bottom side configured for removable attached to the apparatus. The shaft can be configured to move up and down, or sideways. The cover can be made from silicone. The body can be in form of two arms that extend on each side of the shaft. The shape of the cavity can change at the shaft moves.

DETAILED DESCRIPTION OF THE INVENTION

Provided is an apparatus that can generate different types of motions that a user may sexually desire. The apparatus can generate both a rocking and a thrusting motion, in addition to vibratory sensation. As configured, the apparatus generates both thrusting and rocking motions at all times, and the user can choose the desired motion by addition of an appropriate extension. The extension is typically an object resembling a penis (dildo).

Figure 1:
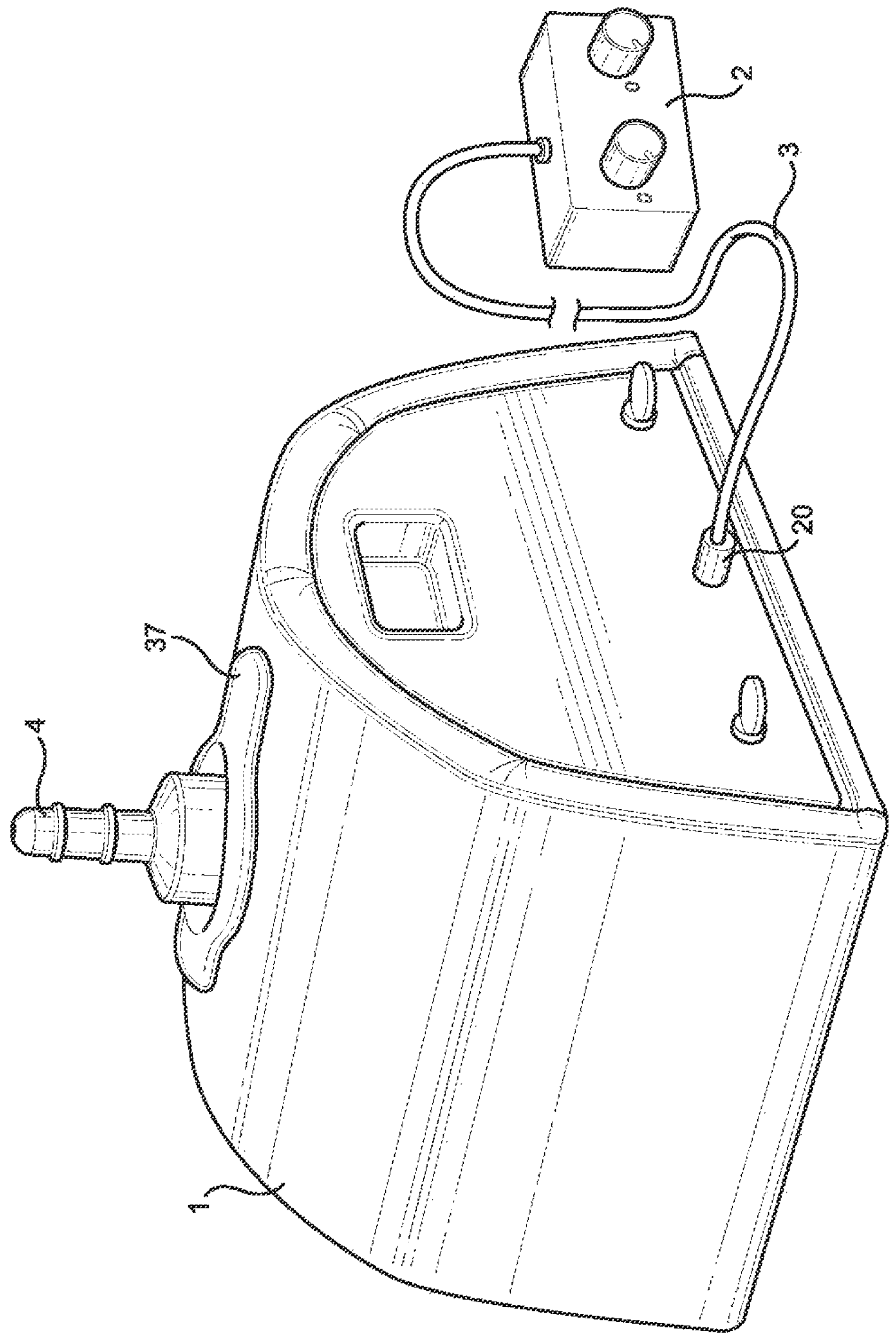
FIG. 1 illustrates a perspective view of the apparatus.

FIG. 1 illustrates a perspective view of the apparatus with external cover. The apparatus has cover 1, inside of which a motor 5 and other components are placed. On top of the apparatus, extension 4 comes out, which is configured to penetrate an individual. Cover 1 is curved on top and shaped like an inverted-U so a person can sit on cover 1. Cover 1 can have a port 20 for attaching to an external device, like a remote control, through a wire 3. Alternatively, a wireless connection via Bluetooth can be made. Remote control 2 can have two or three knobs for adjusting different motions, including rocking, thrusting, and/or vibration. Instead of a remote control, a Bluetooth or other wireless communication can be used to change the setting of the apparatus. For example, a user can use an APP (application/computer program) in a smart phone to change the setting of the apparatus. The apparatus can also have wire (not illustrated) for plugging to an outside source of electricity, typically an AC source of power.

Figure 2:
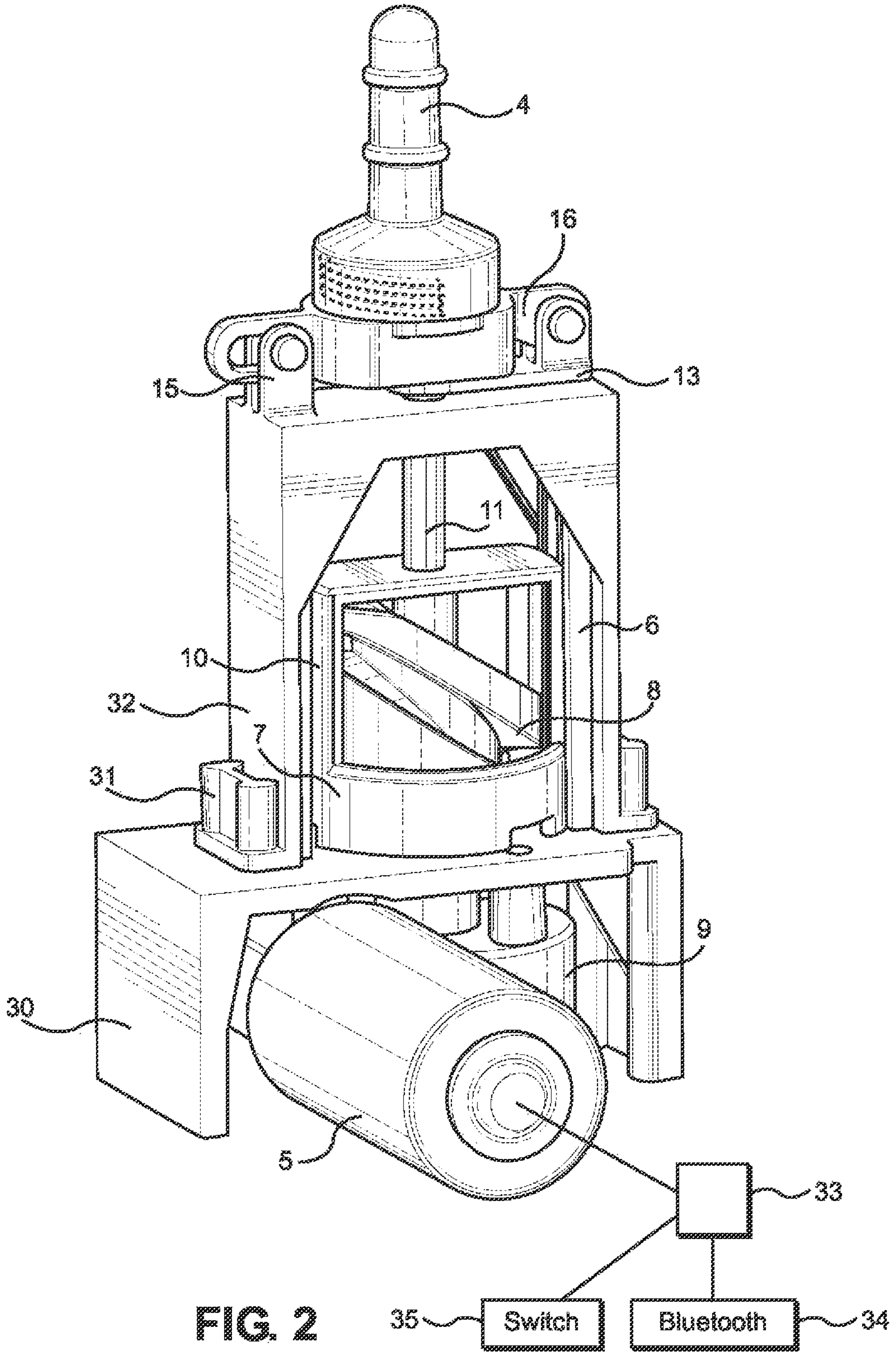
FIG. 2 illustrates a perspective view of the apparatus without external cover.

FIG. 2 illustrates a perspective view of the apparatus without external cover 1. Positioned on the bottom of the apparatus is motor 5 for generating a rotary motion. The motor 5 can be mechanically linked to gear box 9 for reducing the RPM (Revolutions Per Minute). Gear box 9 is mechanically connected to cam 7. As illustrated, cam 7 is made from two parts that snap together. Alternatively, Cam 7 can be made from a single piece of fabricated material. The mechanical motion of motor 5 is transferred through gear box 9 to cam 7, resulting in rotation of Cam 7. Cam 7 has a groove 8 on the exterior that goes all around cam 7. Slider 10 has a guide portion 36 that rides in groove 8. Since groove 8 goes from bottom to top and then top to bottom of cam 7, slider 10 goes up and down as cam 7 rotates around a central axis. Slider 10 goes up and down along rail frames 6. Rail frames 6 are position on each side of slider 10. Positioned above slider 10 is connector 11 (first member), which is in shape of a rod. As slider 10 goes up and down, so does connector 11. Movement of the connector and the extension are provided in detail in FIGS. 3 and 4.

FIG. 2 also illustrates the structure of the apparatus. A support structure 30 with two vertical posts and a horizontal top is placed on the bottom of the apparatus. The motor and gear box are placed below the horizontal top of support structure 30. A second support structure 32 that is narrower and taller is placed on top of the bottom support structure 30. Fasteners 31 are use to attach the support structures 30 and 32 to each other. Two parallel rails 6 are each attached to inside of one the verticals post of the top support structure 32. The cam 7 and the slider 10 are placed below the horizontal portion of support structure 32. An opening exists on top of bottom support structure 30 to mechanically connect cam 7 to gear box 9. The horizontal portion of the top support structure 32 also has an opening for passage of connector 11, shown in form of a rod. The horizontal portion of the top support structure 32 also serves as an attachment point for joint 15, limiting the vertical movement of receiver 16.

Motor 5 can be connected to control box 33, which can house electronic components like a processor, memory, and a power management unit. A Bluetooth chip 34 can also be included to allow the apparatus to receive instructions in a wireless fashion. Switch 35, which can be internal and/or external, can also turn on and off the apparatus.

Figure 3B:
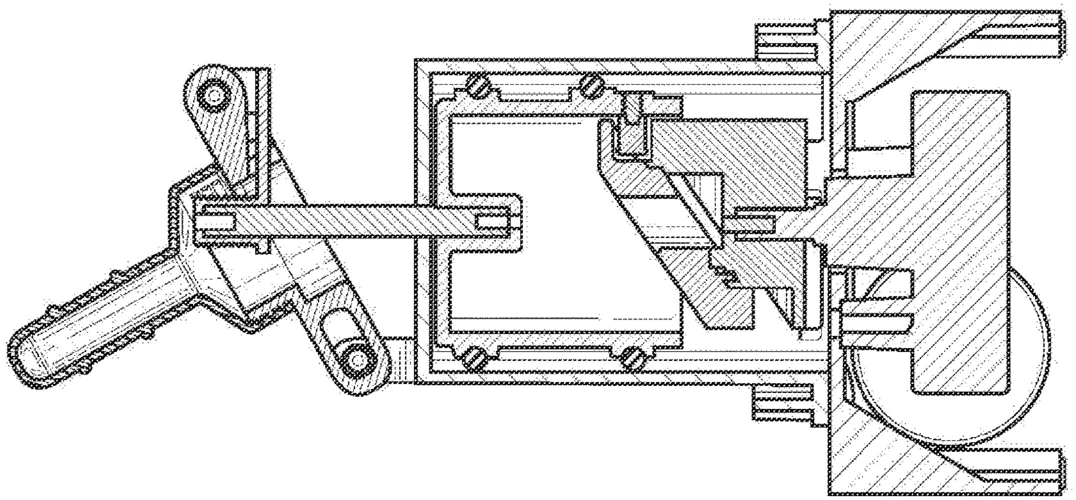
FIG. 3B illustrates the apparatus working with an extension that moves in a rocking fashion.
Figure 3A:
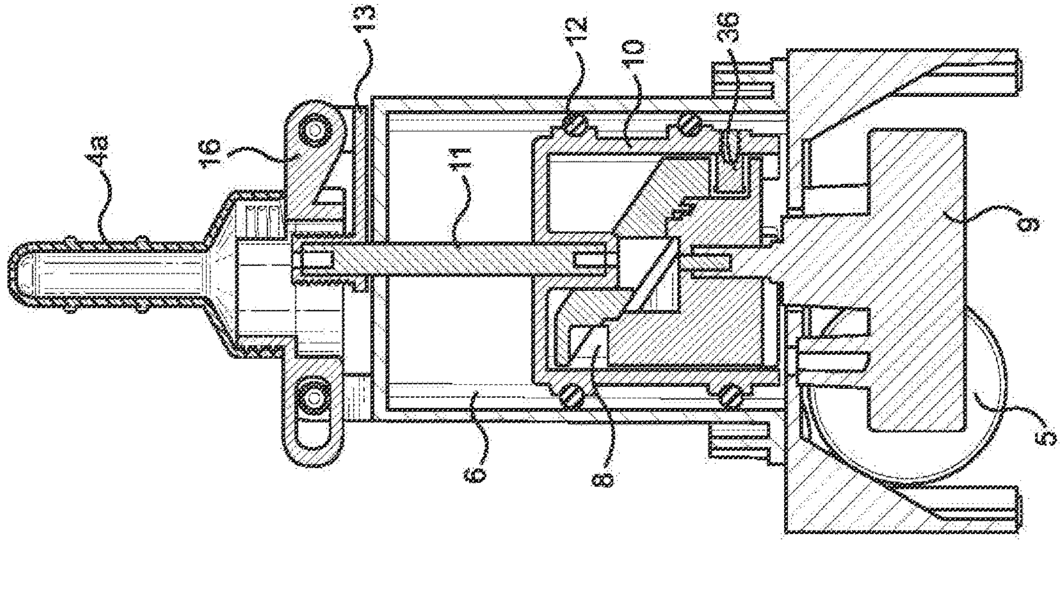
FIG. 3A illustrates the apparatus working with an extension that moves in a rocking fashion.

FIGS. 3A and 3B illustrate the apparatus working with extension 4*a*, which has a large circular bottom. In FIG. 3A, groove guide 36 is at bottom of cam 7. In FIG. 3B, after the cam has rotated 180 degrees, groove guide 36 is on top of cam 7. Groove guide's 36 movement also moves up slider 10 with help of rail slider 12 along two rails 6 positioned opposite of each other. As illustrated in FIG. 3B, upward movement of slider 10 results in elevation of connector 11, which elevates extension 4*a*. Connector 11 makes an up/down motion. Extension 4*a* has a large bottom, and makes a rocking motion, by being elevated more on one side than the other (tilted or pivoted), and moving forward and back, where in the back position the bottom of extension 4*a* is in a horizontal plane.

Figure 4B:
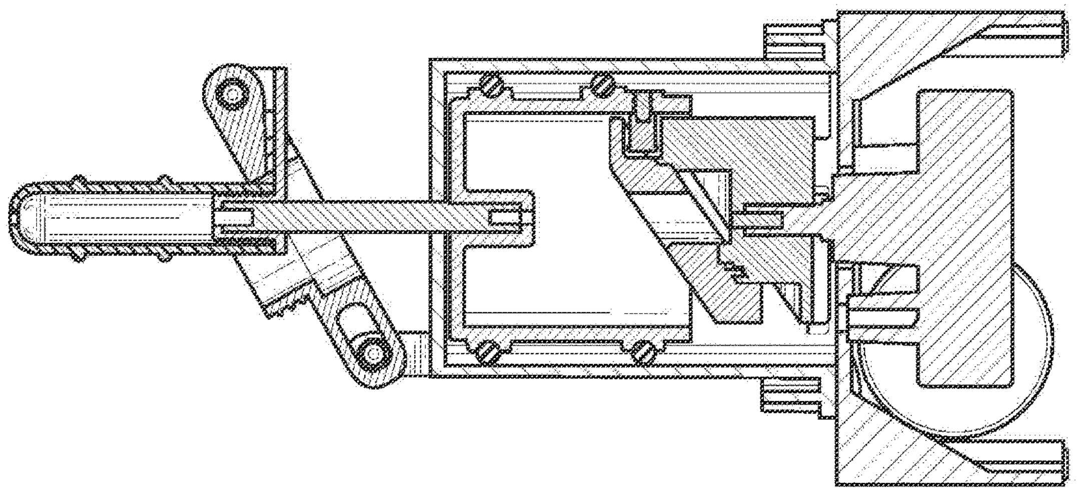
FIG. 4B illustrates the apparatus working with an extension that moves in a thrusting (up and down) fashion.
Figure 4A:
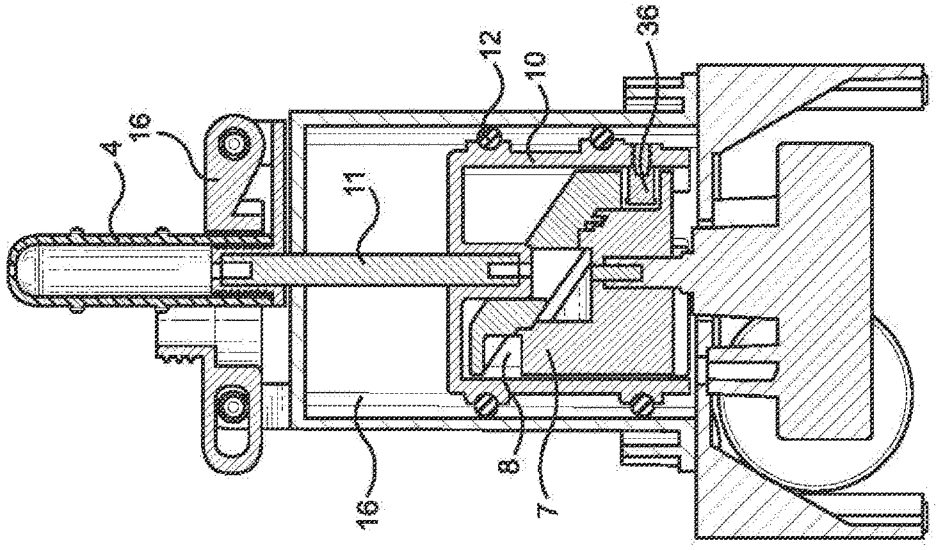
FIG. 4A illustrates the apparatus working with an extension that moves in a thrusting (up and down) fashion.

FIGS. 4A and 4B illustrate the apparatus working with extension 4*b*, which has a uniform diameter, lacking a larger circular base. Extension 4*b* is attached directly to connector 11. In FIG. 4A, groove guide 36 is at bottom of cam 7. In FIG. 4B, after the cam has rotated 180 degrees, groove guide 36 is on top of cam 7. Groove guide's 36 movement also moves up slider 10 with help of rail slider 12 along two rails 6 positioned opposite of each other. As illustrated in FIG. 4B, upward movement of slider 10 results in elevation of connector 11, which elevates extension 4. Connector 11 makes an up/down motion.

Figure 5:
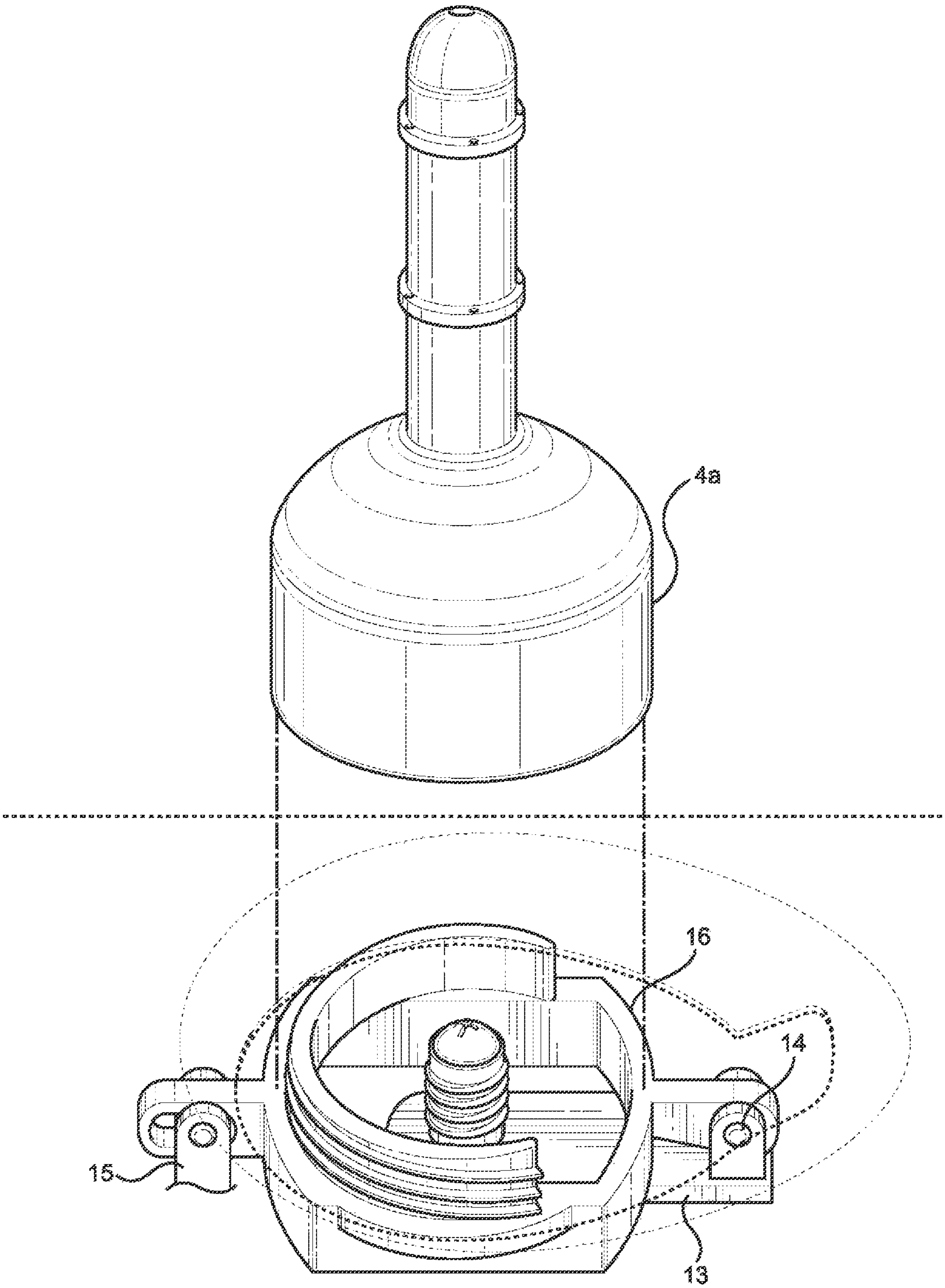
FIG. 5 illustrates attachment of an extension for rocking motion to a receiver on top of an apparatus.

FIG. 5 illustrates attachment of extension 4/4*a* to receiver 16 (second member). Receiver 16 can have threading or receive extension 4 with a snap-on mechanism. Receiver 16 is attached to the internal structure of the apparatus with joint 15. Joint 15 is made of an extension that comes up from top of support structure 32 that is fixed in place and receiver 16. Receiver 16 has a void to which top of support structure 32 is attached. The void has a gap/space to allow for limited movement of receiver 16 relative to top of support structure 32. Receive 16 is configured to pivot/tilt towards joint 15. The other side of receiver is attached through joint 14 to base 13. Joint 14 is not fixed in place, and is configured to move vertically upward and inward towards joint 15 since joint 15 is fixed in place. Below joint 14, base 13 is placed. Base 13 has an opening through which connector 11 transverses. Base 13 is fixed in a horizontal fashion to connector 11. When connector 11 moves up, base 13 remains horizontal, forcing receiver 16 to tilt towards joint 15. Since extension 4*a* is attached to receiver 16, extension 4*a* also tilts with receiver 16, creating a rocking motion.

Figure 6:
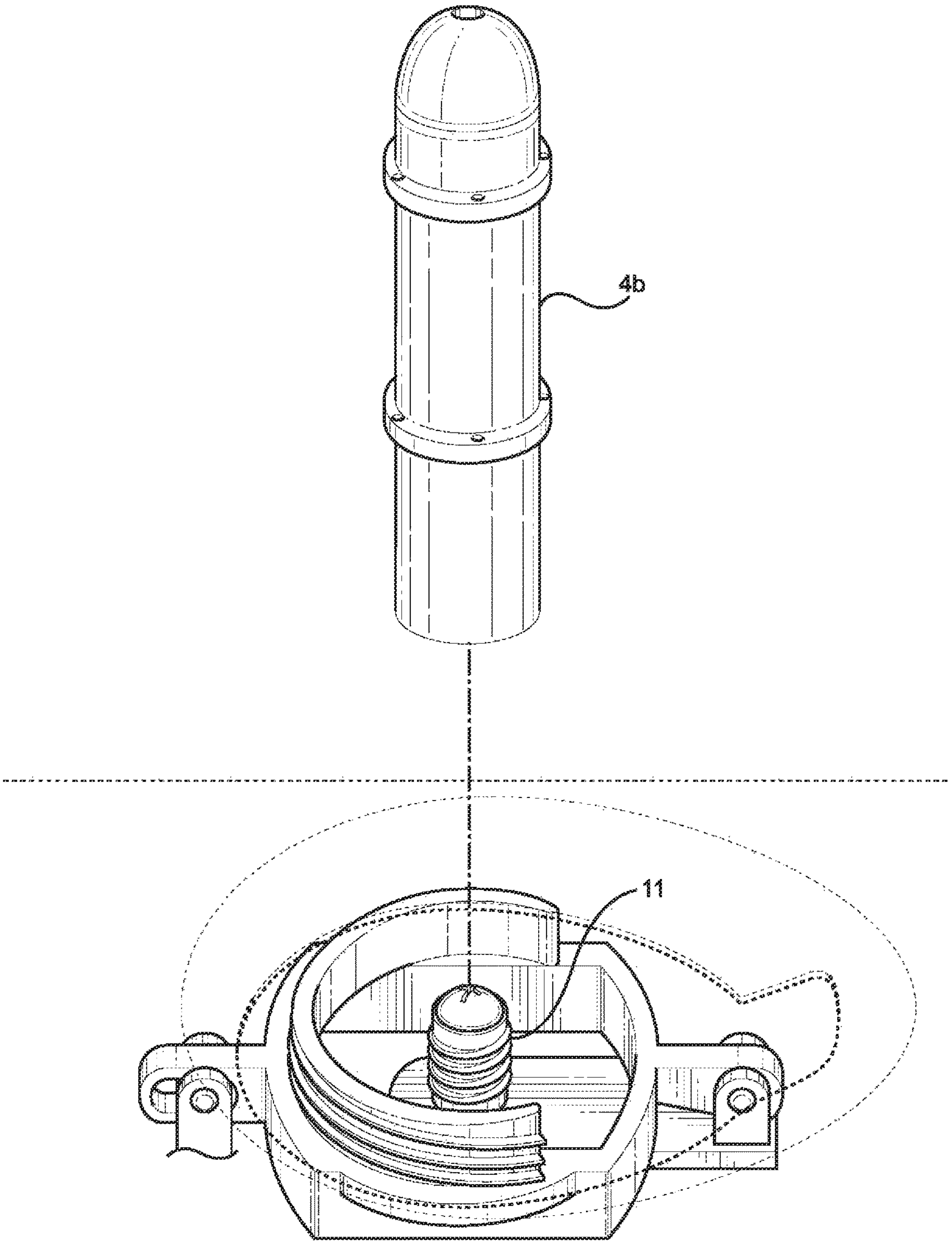
FIG. 6 illustrates attachment of an extension for thrusting motion to a receiver on top of an apparatus.

FIG. 6 illustrates attachment of extension 4/4*b* to receiver 16. Extension 4/4*b* attaches to the top of connector 11. The attachment can be with threading or a snap on mechanism. Since connector 11 moves up and down, extension 4*b* also moves up and down. Extension 4*b* does not do a rocking motion. The receiver 16 still does a rocking motion, however, with no extension attached thereto, the user does not feel the rocking motion. The apparatus performs the same motion regardless of which extension is attached to the apparatus. A user can feel the rocking or up and down motion depending on the extension the user attaches to the apparatus.

Figure 7:
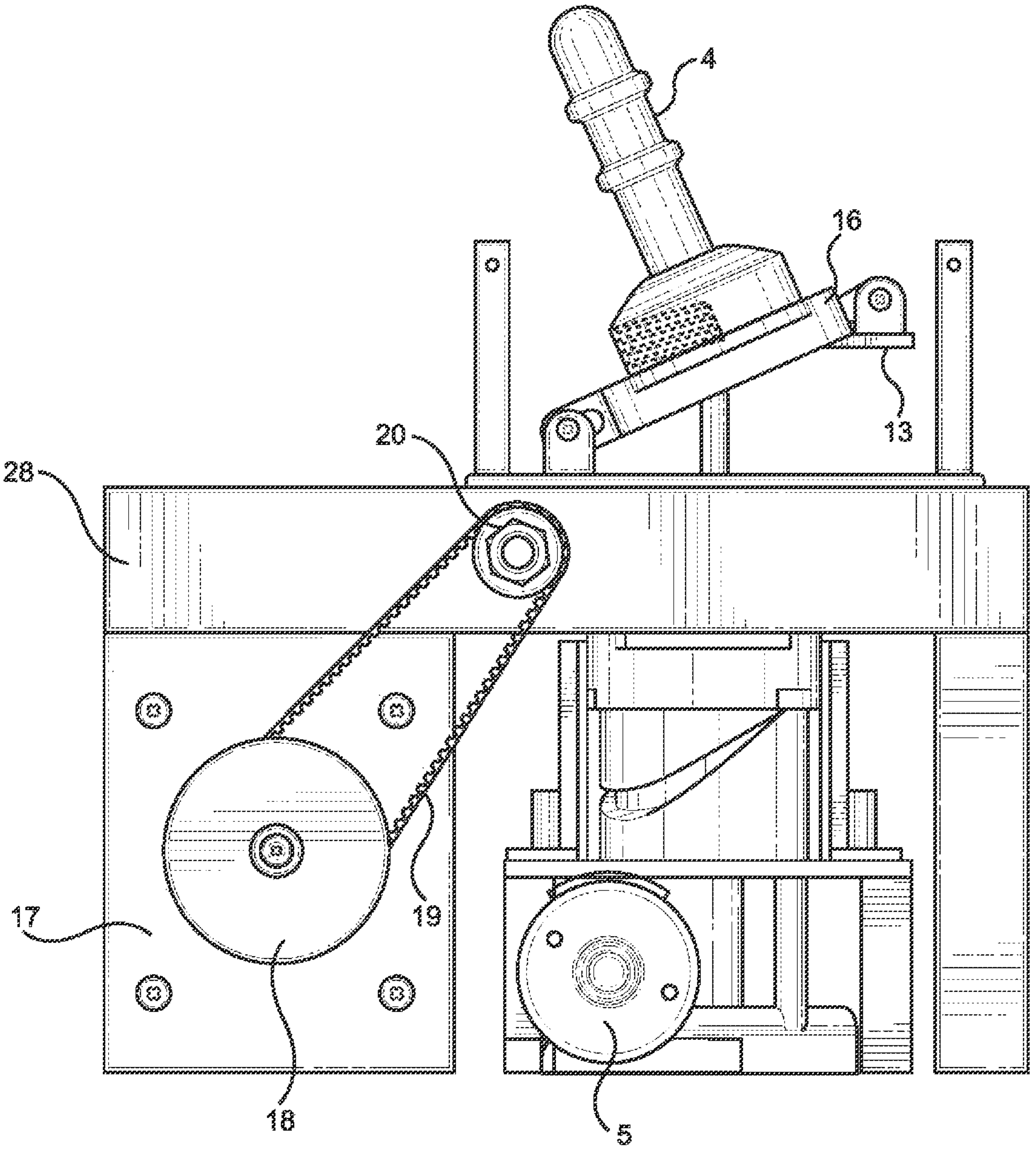
FIG. 7 illustrates a side view of the apparatus, particularly the mechanism to produce a vibrational motion.
Figure 8:
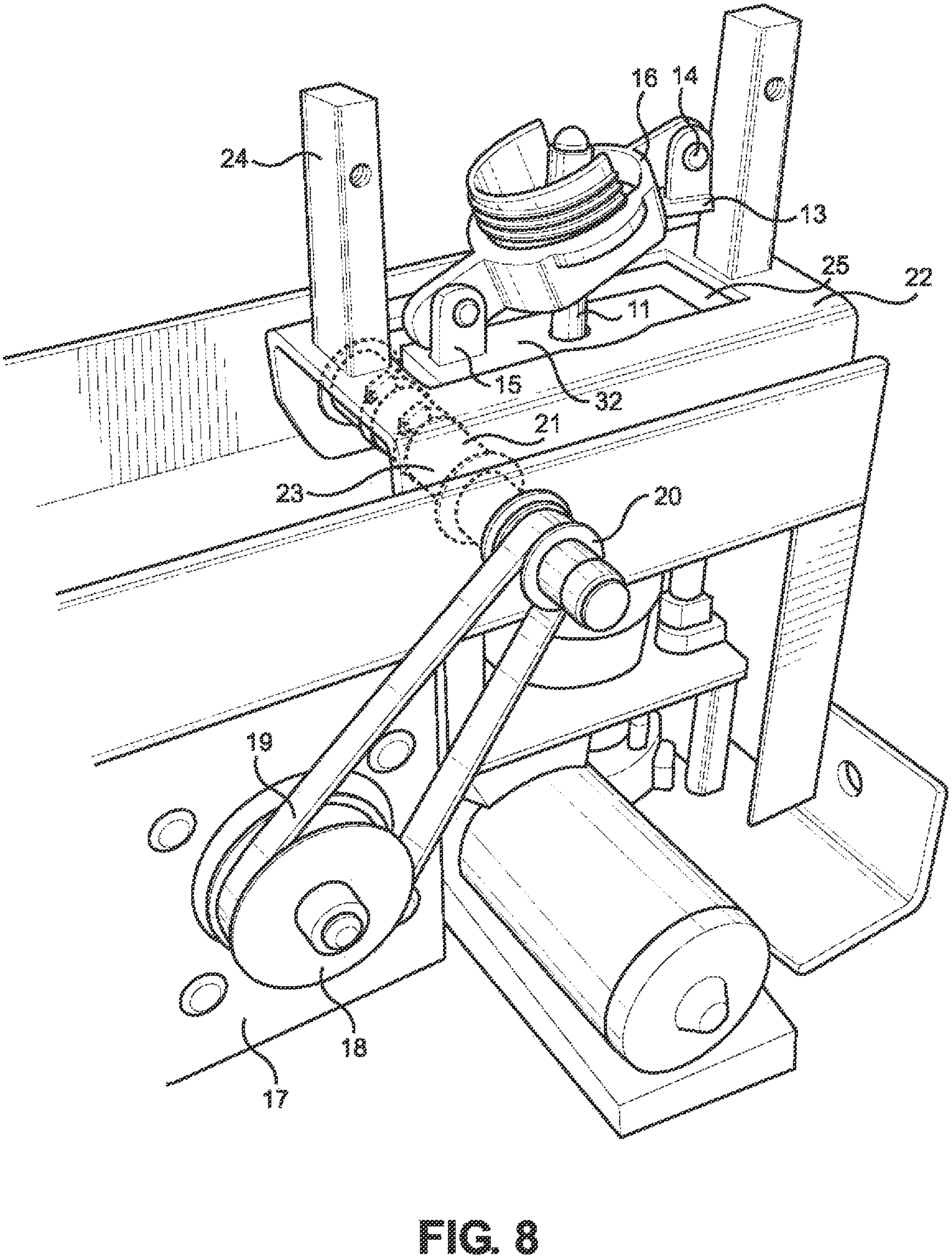
FIG. 8 illustrates a perspective view of the apparatus and the mechanism for generating a vibratory motion.

FIGS. 7 and 8 illustrate a vibrator motor 17 for producing a vibrational motion. The apparatus uses a separate motor 17 for producing a vibrational motion. The motor 17 turns a wheel 18 that is mechanically attached to the motor 17. The wheel 18 is then connected with chain 19 to a roller 20. As the wheel 18 turns, so does the roller 20, albeit with a higher RPM due to a lower diameter. The roller 20 is attached to a shaft 21 that rotates when the roller 20 rotates. The shaft 21 goes through two openings 23 in frame 22. Frame 22 rests on other side on housing 28, and starts vibrating as shaft 21 rotates/turns.

Frame 22 is oriented in a horizontal plane and has vertically oriented sides. Openings 23 are on the vertical sides of frame 22. As shaft 22 spins/rotates, it makes frame 22 move, resulting in a vibrating motion. On top of frame 22, on opposite sides, are supports 24, which are shown as vertical beams. Cover 1 is placed on support 24. Frame 22 has an opening 25 in the horizontal plane. Top of support structure 32 is placed immediately below opening 25. Connector 11 transverses from below opening 25 of frame 22 to top of opening 25. Base 13 and receiver 16 are on the same level or above opening 25. Extension 4 is placed above opening 25.

FIG. 8 also illustrates housing 28 of the apparatus. Housing 28 has a platform for placing frame 22. Motor 5, Motor 17 and gear box 9 are placed below the platform of housing 28. The working components below connector 11 are all placed below platform of housing 28. Connector 11 transverses housing 28 from below to top of platform through an opening in the platform.

Figure 9:
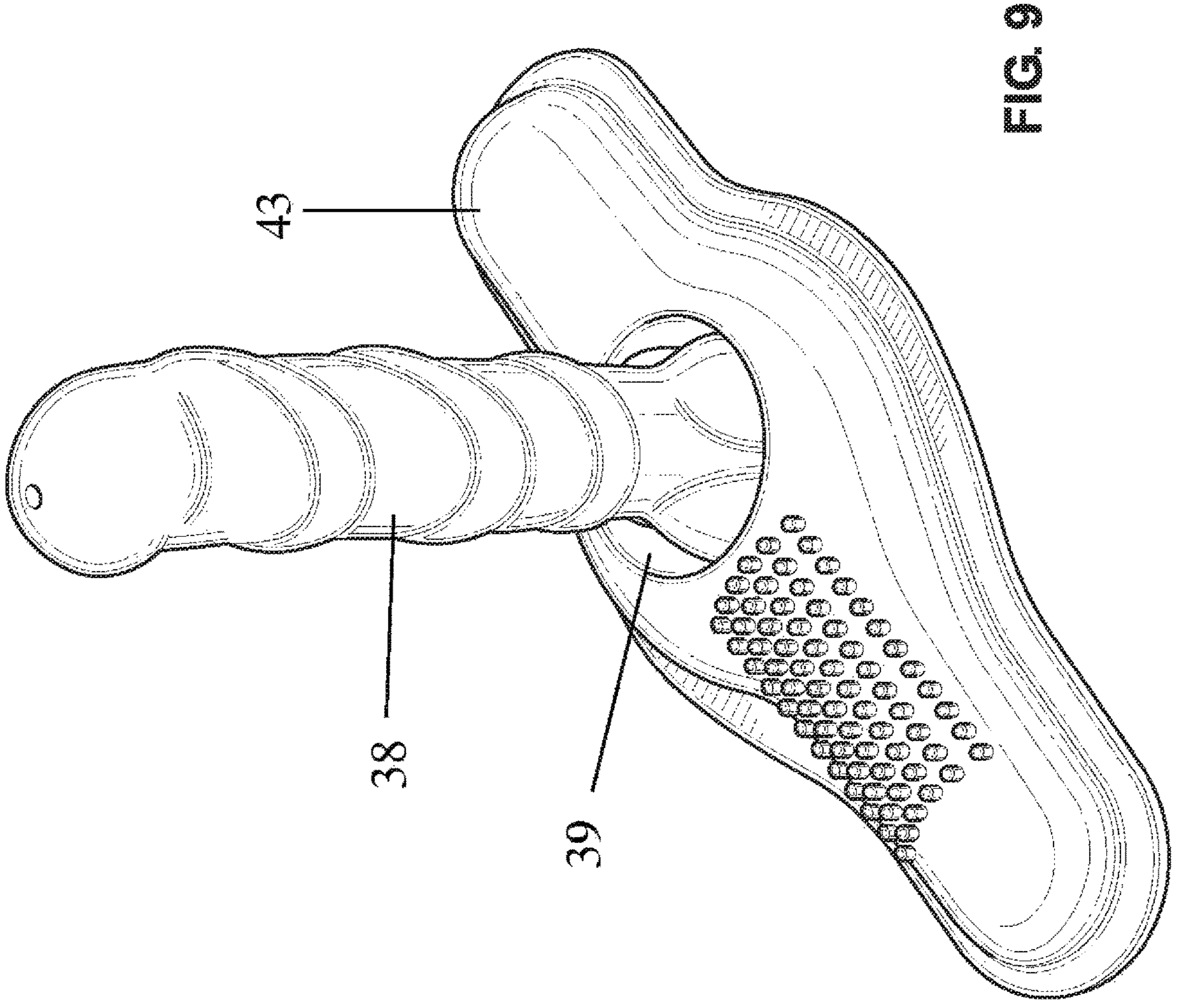
FIG. 9 illustrates a attachment/cover that is placed on top of the apparatus.
Figure 10:
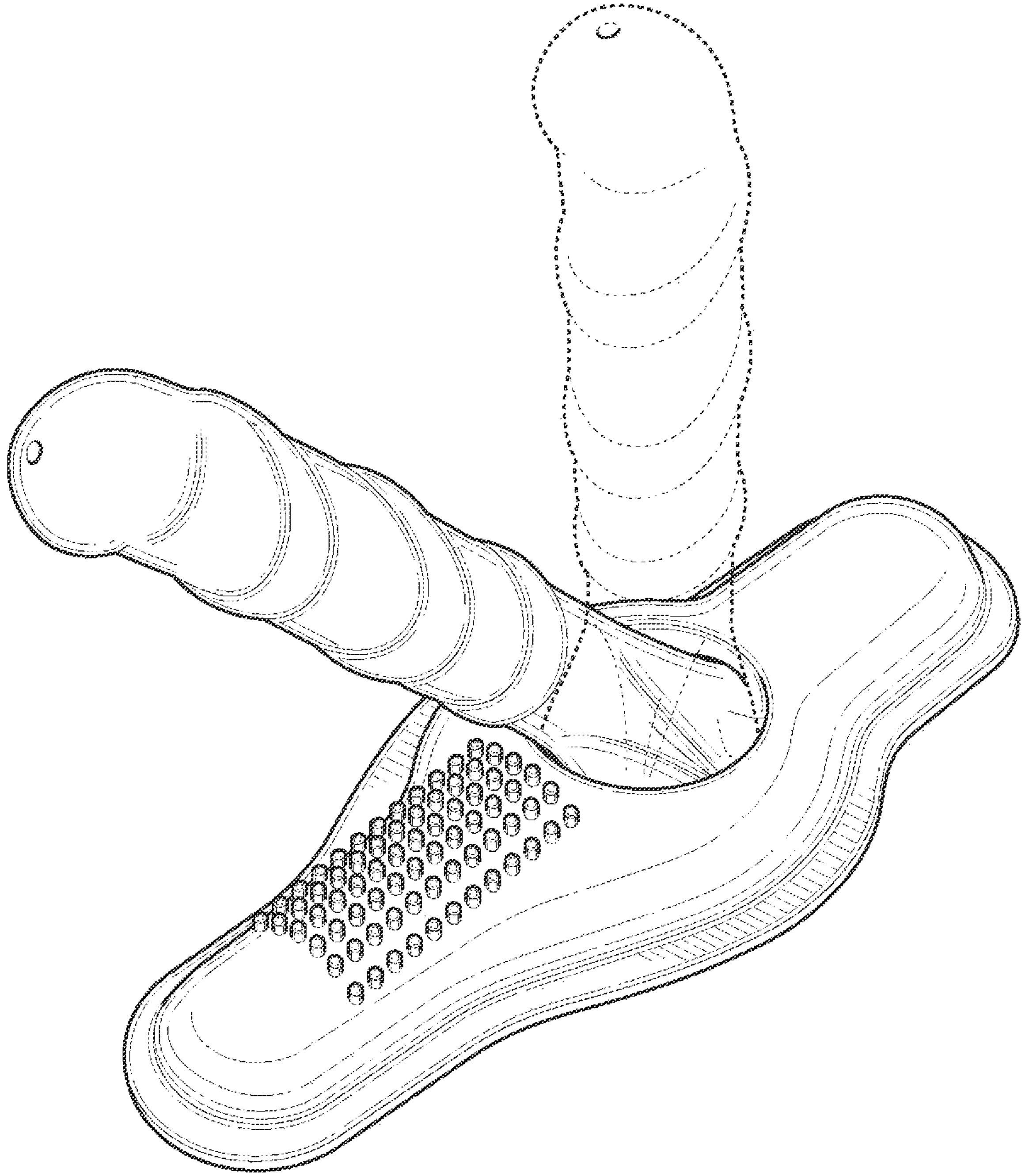
FIG. 10 illustrates movement of the shaft of the cover in a lateral fashion.
Figure 11:
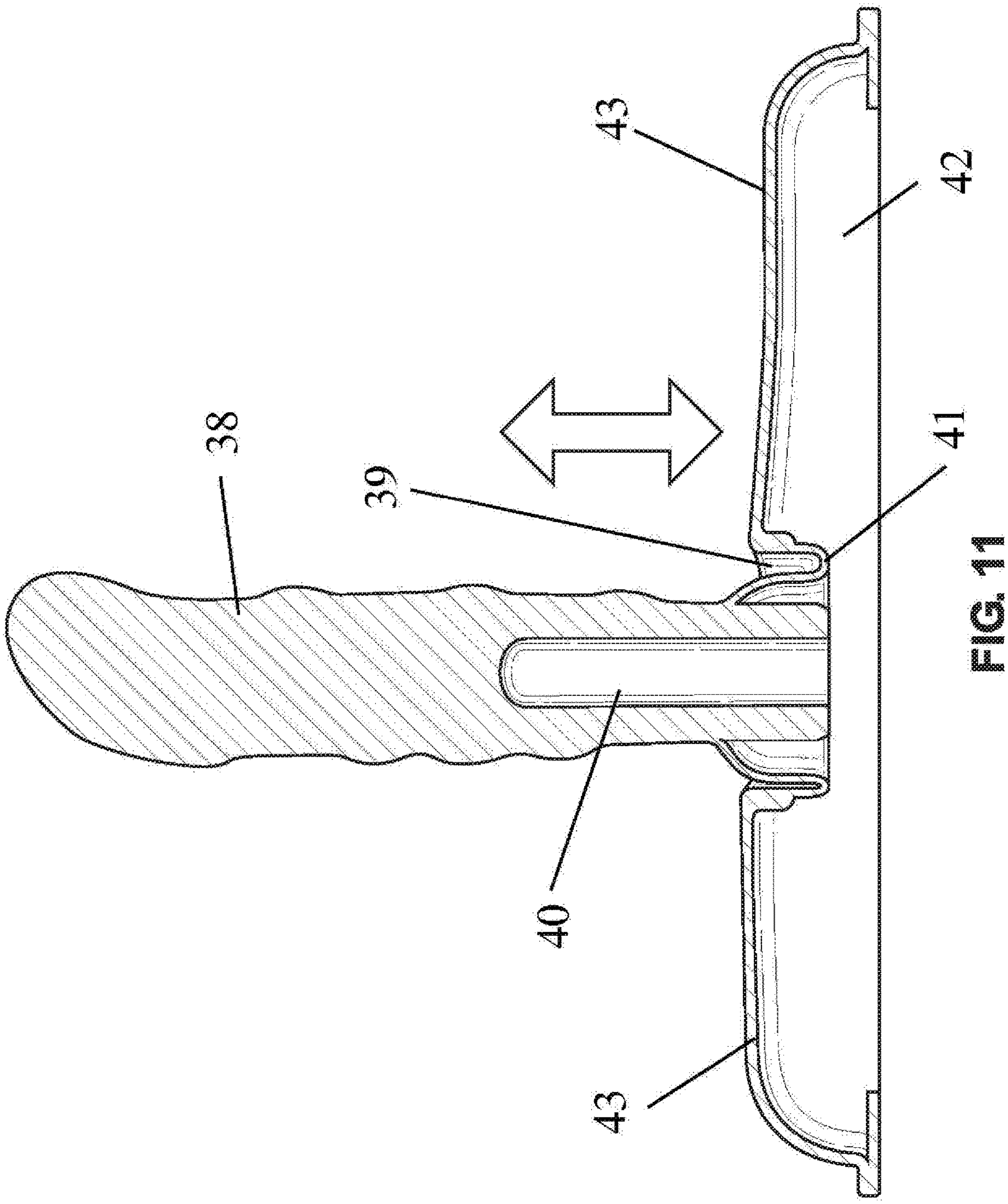
FIG. 11 illustrates movement of the shaft of the cover in a vertical fashion.

FIGS. 9-11 illustrates a silicone cover/attachment 29 that is placed on top of cover 1 and extension 4. The top of cover 1 has a receiver 37 that is configured to receive the bottom surface of silicone cover 29. Silicone cover 29 snaps into place on top of the receiver 37 of cover 1. Silicone cover 29 also has a shaft 38 that penetrates a user. Inside the shaft an opening exists which is configured to receive the attachment 4. The attachment 4 can have an opening on top to allow for exchange of air during placement and removal of the cover 29. Cavity 39 is formed around the base of the shaft 38. The cavity wall 41 is flexible, and is movable. As shaft 38 moves up or down, or forward and back, the cavity wall 41 moves (changes in shape) to accommodate for the movement. The thickness of cavity wall 41 can be less than the thickness of other parts of cover 29. On each side of cavity 39 there can be arms 43 that extend out. Under arms 43 there can be a snap cavity 42 for snapping cover 29 on top of the apparatus. As illustrated in FIGS. 9-11, wall 41 of cavity 39 starts at the bottom of shaft 38. The wall 41 has a straight portion and then moves up, in a circular fashion all around the base of shaft 38. The top of the wall 41 is attached to top of the arms on each side of the cavity 39. Under the top of the arms 43, a snap cavity 42 can exist for snapping the cover onto the apparatus.

1. Cover
2. Remote control
3. wire (from remote)
4. Extension
5. Motor
6. Rail
7. Cam
8. Groove
9. Gearbox
10. Slider
11. Connector
12. Rail Guide
13. Base
14. Joint (not attached)
15. Joint (attached)
16. Receiver
17. Vibration motor
18. Wheel
19. Chain
20. Roller
21. Shaft
22. Frame
23. Frame openings (vertical)
24. Support
25. Frame opening (horizontal)
28. Housing
29. Silicone attachment/cover
30. Bottom support structure
31. Fastener
32. Top support structure
33. Control box
34. Bluetooth
35. Switch
36. Groove Guide
37. Receiver (on top of cover)
38. Shaft
39. Cavity
41. Cavity wall
42. Snap Cavity
43. arms

What is claimed is:

1. A cover for an apparatus configured to produce a motion; the cover comprising:
a) a shaft;
b) a body in form of two arms that extend on each side of the shaft; and
c) a cavity all around the shaft, and in between the shaft and the body;
wherein the shaft is movable in relation to the body when a force is applied to the shaft from a bottom of the cover.

2. The cover of claim 1, wherein the shaft has an opening inside that is configured to receive a portion of the apparatus.

3. The cover of claim 1, wherein the body has a snap cavity on a bottom side configured for removable attached to the apparatus.

4. The cover of claim 1, wherein the shaft is configured to move up and down, or sideways.

5. The cover of claim 1, wherein the cover is made from silicone.

6. The cover of claim 1, wherein shape of the cavity changes as the shaft moves.

7. An apparatus for producing a motion to be felt by a user comprising;
a) a motor for generating a motion;
b) a first member mechanically coupled to the motor, the member configured to have a motion of up and down; and
c) a second member mechanically coupled to the first member and attached to a fixed location on the apparatus, the second member configured to tilt as a result of the motion of the first member;
d) an extension attached to the first or the second member;
e) a cover placed on top of the extension, the cover having a shaft, a body, and a cavity all around the shaft, the shaft having an opening for receiving the extension;

wherein the user has an option of attaching the extension to the first member to experience the up and down motion generated by the first member or attaching the extension to the second member to experience the tilting motion generated by the second member, wherein the extension attached to the first or the second member can be same or different extension.

8. The apparatus of claim 7, wherein the shaft has an opening inside that is configured to receive a portion of the apparatus.

9. The apparatus of claim 7, wherein the body has a snap cavity on a bottom side configured for removable attached to the apparatus.

10. The apparatus of claim 7, wherein the shaft is configured to move up and down, or sideways.

11. The apparatus of claim 7, wherein the cover is made from silicone.

12. The apparatus of claim 7, wherein the body is in form of two arms that extend on each side of the shaft.

13. The apparatus of claim 7, wherein shape of the cavity changes as the shaft moves.

14. An apparatus for producing a motion to be felt by a user comprising;

a) a motor for generating a motion;

b) a cam having a groove, the cam mechanically coupled to the motor, the cam rotating as a result of motion from the motor, c) a slider mechanically coupled to the cam, the slider moving up and down as the cam rotates;

d) a rod attached to the slider, the rod moving up and down with the slider, wherein the rod moves up and down as the motor generates motion; and e) an extension attached directly or indirectly to the rod, the extension having an up and down motion in case of direct attachment and a tilting motion in case of indirect attachment;

further comprising a cover placed on top of the extension, the cover comprises a shaft, a body, and a cavity all around the shaft, the shaft having an opening for receiving the extension;

wherein the user experiences the up and down motion or the tilting motion generated by the extension.

* * * * *